United States Patent [19]
Ishiguro

[11] Patent Number: 6,108,439
[45] Date of Patent: Aug. 22, 2000

[54] ULTRASOUND IMAGE PROCESSING SYSTEM

[75] Inventor: Masaaki Ishiguro, Omiya, Japan

[73] Assignee: Fuji Photo Optical Co., Ltd., Omiya, Japan

[21] Appl. No.: 08/880,348

[22] Filed: Jun. 24, 1997

[30] Foreign Application Priority Data

Jun. 26, 1996 [JP] Japan .................................. 8-184289

[51] Int. Cl.⁷ .................................................. G06K 9/00
[52] U.S. Cl. ........................................ 382/131; 382/154
[58] Field of Search ........................... 382/131; 128/916, 128/653.1, 660.09

[56] References Cited

U.S. PATENT DOCUMENTS

| | | | |
|---|---|---|---|
| 5,361,768 | 11/1994 | Webler et al. ........................... | 128/916 |
| 5,765,561 | 6/1998 | Chen et al. ............................. | 128/653.1 |
| 5,771,895 | 6/1998 | Slager ..................................... | 128/916 |
| 5,817,019 | 10/1998 | Kawashima ............................. | 128/916 |
| 5,842,473 | 12/1998 | Fenster et al. ......................... | 128/660.09 |

*Primary Examiner*—Jose L. Couso
*Assistant Examiner*—Shawn Cage
*Attorney, Agent, or Firm*—Oblon, Spivak, McClelland, Maier & Neustadt, P.C.

[57] ABSTRACT

An ultrasound image processing system, having an ultrasound image capture device such as a B-mode ultrasound probe capable of making 2D scans over a predetermined range, and a drive for moving an ultrasound transducer in a direction different from the direction of 2D scans by the transducer to capture 2D ultrasound images sequentially in a predetermined pitch in the direction of movement of the ultrasound transducer. The ultrasound image processing system is provided with a marker for inserting a marker sign on field images selected from a large number of 2D ultrasound images sequentially captured by the image capture device, for use in three-dimensional image processing in a subsequent stage.

12 Claims, 6 Drawing Sheets

ULTRASOUND IMAGE PROCESSING SYSTEM

BACKGROUND OF THE INVENTION

1. Field of the Art

This invention relates generally to an ultrasound image processing system for generating and displaying three-dimensional ultrasound images on the basis of a series of sequentially captured two-dimensional tomographic ultrasound images, and more particularly to an ultrasound image processing system having a marker means for marking and distinguishing two-dimensional ultrasound images, which are fundamentally necessary for three-dimensional image processing, from other 2D ultrasound images captured.

2. Prior Art

In ultrasound examination, ultrasound signals are transmitted into patient body through an ultrasound transducer, while thereby receiving return echo signals from body tissues at different depths in the directions of signal transmission. The return echo signals are processed into video signals to display ultrasound images on a monitor screen. A two-dimensional tomographic ultrasound image (hereinafter referred to as "2D ultrasound image" for brevity) is obtained by an ultrasound scan over a predetermined range, that is to say, by a B-mode ultrasound scan of a plane section. A large number of 2D ultrasound images of different plane sections, which are captured successively by shifting the scan position in a certain pitch in a predetermined direction, can be converted into a three-dimensional ultrasound image (hereinafter referred to as "3D ultrasound image" for brevity) through image processing operations. Needless to say, as compared with 2D ultrasound images, 3D ultrasound images displayed on a viewing screen are more helpful in clearly grasping the internal tissue structures of scanned regions, and contribute to enhance the accuracy of ultrasound examinations.

A series of 2D ultrasound images, which are each expressed on a 2D X-Y coordinate system, come to have expressions of spatial expanse when lined up along Z-axis of a 3D X-Y-Z coordinate system. In ultrasound images, echoes from internal tissue structures are converted into different light intensities and expressed as variations in luminance on a viewing screen. Therefore, internal tissue structures can be displayed as a 3D image by implementing picture data between adjacent 2D ultrasound images, through linear interpolation based on luminance levels of picture signals in preceding and succeeding 2D ultrasound images. Further, internal tissue structures can be displayed as 3D ultrasound images by dissolving a 3D space on a 3D coordinate system into voxels which contain the luminance information in the entire 3D space scanned. Images of an organ or internal tissue structures of particular interest can be extracted and displayed by image processing based on 3D picture signals.

Any way, in either type of the above-mentioned 3D picture images, a delimited 3D space is set up in a particular intracorporeal region of interest by way of the scan range of 2D ultrasound picture images and the direction of alignment of the ultrasound picture images, for the purpose of displaying internal tissue structures or an internal organ in that space in a 3D perspective view. In order to acquire picture data for 3D images of this sort, it is necessary to produce all the luminance information throughout that 3D space, namely, to create correlated picture data for and between N-number of 2D ultrasound images captured throughout that space. Therefore, 3D ultrasound image processing normally involves a vast amount of picture data and involves extremely complicate data processing operations which take time even by a large-scale data processor.

In this regard, in an attempt to make it possible to observe 3D ultrasound images of internal tissues quickly on a monitor screen, the inventor developed an inexpensive 3D ultrasound image processing system which can produce 3D ultrasound images through simplified signal processing operations, as disclosed in his U.S. Pat. No. 5,682,295 (hereinafter referred to as "patent" for brevity).

More specifically, according to the 3D ultrasound image processing system of the above-mentioned patent by the inventor, in order to permit three-dimensional grasping of a subject under observation, a 3D ultrasound image is built on X-, Y- and Z-axes of a three-dimensional coordinate system on the basis of a series of 2D ultrasound images which are obtained by scanning the subject sequentially along Z-axis of the coordinate system in a predetermined pitch. Normally, the resulting 3D ultrasound image is a non-transparent surface image simply showing boundary surfaces of a scanned range without exposing its internal structures to view. From non-transparent 3D ultrasound images of this sort, it is difficult to obtain information on the conditions of internal structures or internal tissues of a scanned subject. In order to expose internal structures to view, part of a 3D ultrasound image is hollowed out by an image cut-out operation at a position of particular interest to display on a monitor screen a cut-out 3D ultrasound image which permits to examine the conditions of internal structures or internal tissues of an organ three-dimensionally through a cut surface or surfaces of the displayed image.

For this purpose, firstly a plural number of 2D ultrasound images, i.e., unit images to be used for 3D image processing, are captured by the use of a known ultrasound imaging system having an ultrasound probe connected to an ultrasound image observation terminal with an ultrasound signal processor and a viewing screen. More specifically, by the use of such an ultrasound imaging system, a subject is scanned sequentially in a predetermined pitch by a B-mode ultrasound probe which is moved in a direction along the subject, to obtain an N-number of 2D ultrasound images as picture data for building up a 3D ultrasound image. For instance, while moving a radial scan ultrasound probe in a linear or axial direction thereof, a series of 2D ultrasound images are captured sequentially in a predetermined pitch or at predetermined intervals to provide unit images to be integrated into a 3D ultrasound image.

The unit images which have been captured in this manner by the use of a 2D ultrasound image processing system are fed to and processed by a 3D image processing system to produce a 3D ultrasound image. In the 3D image processing system, by coordinate conversion, picture data of the 2D ultrasound image are put on X- and Y-axes of a 3D coordinate system, which intersect with each other at an angle of 120°. The coordinate-converted picture data of 2D ultrasound images are then aligned in the direction of Z-axis to build up a 3D ultrasound image of a columnar shape. The columnar 3D ultrasound image which is displayed on a monitor screen consists of three elemental images, i.e., images of two opposite end faces and a circumferential surface of a cylindrical scanned range. Namely, the 3D ultrasound image is of surfaces at outer boundaries of the scanned range, without showing internal structures which exist within the scanned range. Therefore, there arises a need for hollowing out part of the 3D ultrasound image, which is on display on a viewing screen, in a region of particular interest by an image cut-out operation. In the case of a 3D ultrasound image with such a cut-out portion, the elemental images include images of exterior surfaces of a scanned range as well as images of one or more cut surfaces. By changing the cut-out mode or cut position, the shape of an internal organ of particular interest or other internal structures or conditions of internal tissues can be viewed through cut surfaces of the cut-out portion.

Thus, conditions of an internal organ or tissues of particular concern can be observed through the cut surfaces which can be determined arbitrarily. In addition, by changing or shifting the positions of cut surface in 3D ultrasound images, one can grasp three-dimensional expansions of a subject more perfectly. Nevertheless, it is desirable for the 3D image processing system to be able to produce a cut-out 3D ultrasound image of this sort by simple signal processing operations, with quick response not only in signal processing for 3D ultrasound images but also in re-processing picture signals and refreshing a 3D image on display in response to alterations of cut-out mode or position. For this purpose, upon changing a cut-out mode or position, of a plural number of elemental picture images which constitute a 3D ultrasound image or a cut-out 3D ultrasound image, it suffices for the 3D signal processor to compile picture data of only those elemental images which correspond to new cut surfaces, and to paste the elemental images of new cut surfaces in specified positions on an original 3D ultrasound image. Accordingly, a 3D ultrasound image can be generated and refreshed by operations involving an extremely reduced amount of picture data. It follows that 3D ultrasound images can be generated and displayed in a desired cut-out mode quickly in a simplified manner.

Three-dimensional grasping of internal structures of a subject can be realized either by generating voxel data as explained hereinbefore in connection with the prior art by generating a cut-out 3D ultrasound image as in the above-mentioned patent by the present inventor. Whichever is the case, it becomes necessary to capture a large number of 2D ultrasound images sequentially by moving an ultrasound transducer in a direction perpendicular to ultrasound scan planes.

A 3D ultrasound image of high resolution can be obtained by processing picture data of all of captured 2D ultrasound images as unit images for a 3D image to be built up as described above. However, the greater the number of unit images, the larger becomes the amount of picture data to be processed. Accordingly, there may arise a necessity for selecting and extracting a suitable number of unit images for a 3D ultrasound image from numerous 2D ultrasound images captured. Above all, in the case of a 3D ultrasound image processing system as disclosed in the above-mentioned patent by the inventor, for the purpose of simplifying picture data processing for cut-out 3D ultrasound images, it is desirable for an image processing system to have a quick mode which depicts a relatively simple 3D image of internal structures by using only part of captured 2D ultrasound images as unit images, in addition to a fine mode using all of captured 2D ultrasound images to display a 3D ultrasound image of high resolution.

Further, when an ultrasound transducer is moved manually for capturing 2D unit images, there may arise a situation that, due to sluggish movements of the ultrasound transducer, same 2D ultrasound image are outputted from a 2D image capture device repeatedly before a displayed picture image is renewed. The same 2D picture images of this sort have to be removed prior to 3D image processing. Accordingly, in a 3D image processing on the basis of picture data of 2D ultrasound images which have been directly saved in an image recording means from a 2D image capture device, it becomes necessary to extract and distinguish unit images to be used for 3D ultrasound image processing, from other images in a large number of sequentially captured 2D images stored in an image recording means.

In selectively extracting unit images for 3D image processing from a large number of sequentially captured 2D ultrasound images as described above, field images of necessary unit images have to be instantly distinguishable from other field images. In this regard, since each 2D ultrasound image contains data of its own position (position data in the direction of Z-axis), arrangements may be made to extract the necessary unit images on the part of a 3D image processing system. However, it will lead to complication of the 3D processing system and of signal processing operations to be performed by the 3D processing system.

SUMMARY OF THE INVENTION

With the foregoing situations in view, it is an object of the present invention to provide an ultrasound image processing system with a marker means for marking and distinguishing 2D ultrasound images to be used in subsequent 3D image processing, from other 2D ultrasound images which are sequentially captured by real-time ultrasound image capturing.

It is another object of the present invention to provide an ultrasound image processing system which can generate 3D ultrasound images by simplified signal processing operations.

According to the present invention, the above-stated objective are achieved by an ultrasound image processing system which essentially includes: an ultrasound image capture means having an ultrasound transducer capable of making two-dimensional ultrasound scans over a predetermined range, and a transducer drive means for moving the ultrasound transducer in a direction different from direction of two-dimensional ultrasound scans by the ultrasound transducer to capture a large number of 2D ultrasound images sequentially in a predetermined pitch in the direction of movement of the ultrasound transducer; a marker means for inserting marker signs on selected field images among a large number of 2D ultrasound images captured by the ultrasound image capture means; and an image recording means for storing 2D ultrasound images with marker signs along with 2D ultrasound images without marker signs.

As described above, the ultrasound image processing system according to the present invention is composed of at least a 2D ultrasound image capture means, a marker means, and an ultrasound image recording means.

The ultrasound transducer of the 2D ultrasound image capture means is driven to scan 2D planes over a predetermined range and at predetermined time intervals while it is being moved in a direction perpendicular to the planes of 2D ultrasound scans to obtain a large number of sequential 2D ultrasound images for use as picture data in generating a 3D ultrasound image in a subsequent stage. The ultrasound transducer may be either a mechanical scan type or an electronic scan type. The planes of 2D ultrasound scans may be of a linear, radial, sectoral or any other shape as long as they stretch two-dimensionally. A large number of 2D ultrasound images can be captured in a predetermined pitch in a direction perpendicular to the planes ultrasound scans by mechanically moving the ultrasound transducer in that direction. There is no need for moving the ultrasound transducer in case it is an electronic scan type having a matrix of ultrasound transducers.

The 2D ultrasound images sequentially captured by the image capture means in this manner are recorded in the image recording means, which may be a video memory or a memory card provided internally of the image capture means or an external videotape recorder, magnetic disc, photomagnetic disc, optical disc etc. Of these recording devices, a videotape recorder is most preferable from the standpoint of cost.

When recording field image data of 2D ultrasound images captured by the 2D image capture means, unit images or field images which are necessary for subsequent 3D image processing are each stamped with a marker signal by a marker means to distinguish them from other field images in a large number of captured 2D ultrasound images concurrently with the real-time 2D image capturing. For this purpose, the marker means includes an image extractor which selectively extracts field images to be marked, a marker signal generator for generating marker signals of specified marker position and size, and a marker signal synthesizer for synthesizing a marker signal with selectively extracted field images. As a result, when saving sequentially captured 2D ultrasound images in an image recording means, a marker is inserted in a specified position on each one of 2D ultrasound images which are necessary for generation of a 3D ultrasound image.

In this manner, picture data of a large number of 2D ultrasound images are saved in an image recording means, which will be accessed by a 3D image processor for generation and display of a 3D ultrasound image. On such an occasion, marked unit images which are necessary for 3D image processing can be selectively uploaded by way of the shape or position of inserted markers. Therefore, marked unit images which are fundamentally necessary for 3D image processing alone can be unloaded into the 3D image processor, to exclude other field images for the purpose of suppressing data accumulation in the 3D image processor to a minimum to simplify and accelerate signal processing operations for generation of 3D ultrasound images.

BRIEF DESCRIPTION OF THE DRAWINGS

The above and other objects, features and advantages of the invention will become apparent from the following description, taken in conjunction with the accompanying drawings which show by way of example a preferred embodiment of the invention and in which.

DESCRIPTION OF PREFERRED EMBODIMENTS

Figure 1:
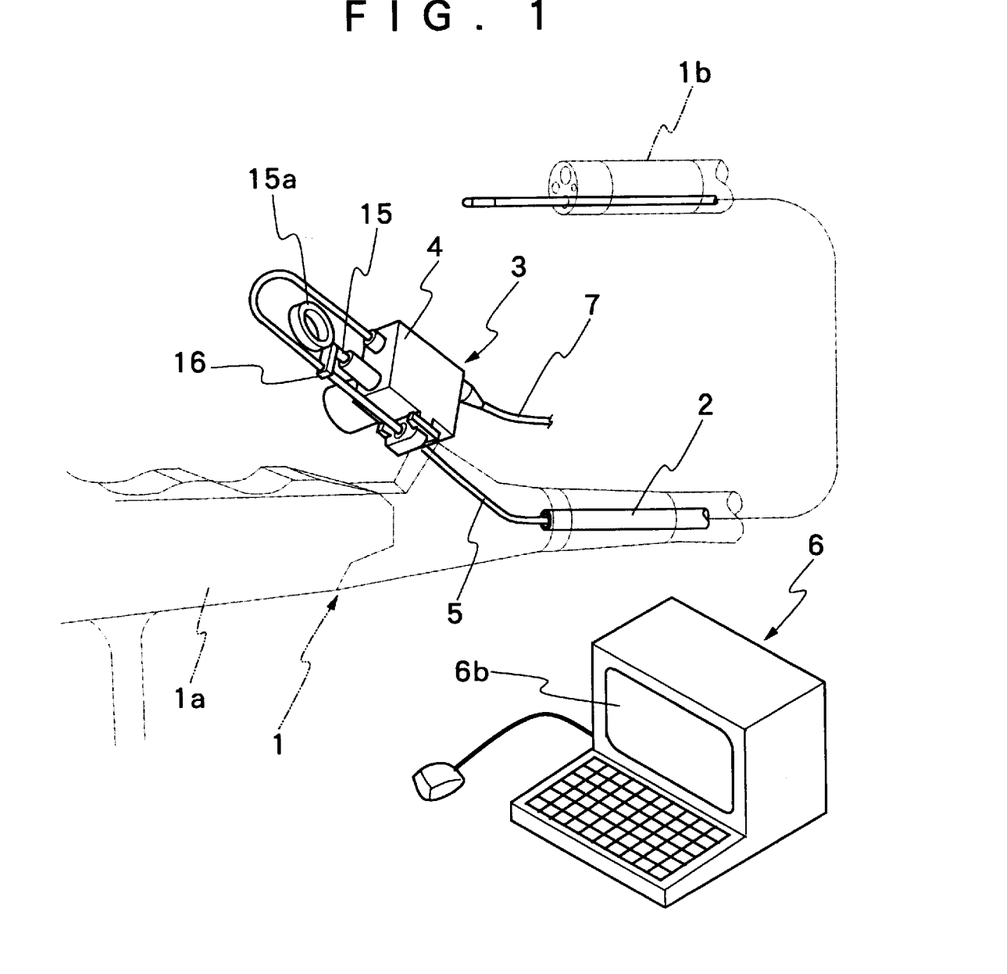
FIG. 1 is a schematic view of a 2D ultrasound image capture device with an endoscopically inserting ultrasound probe.
Figure 2:
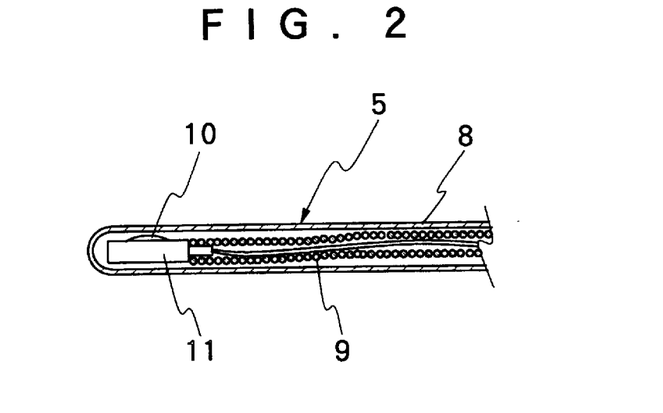
FIG. 2 is a schematic view of a distal end portion of a catheter member of the ultrasound probe.
Figure 3:
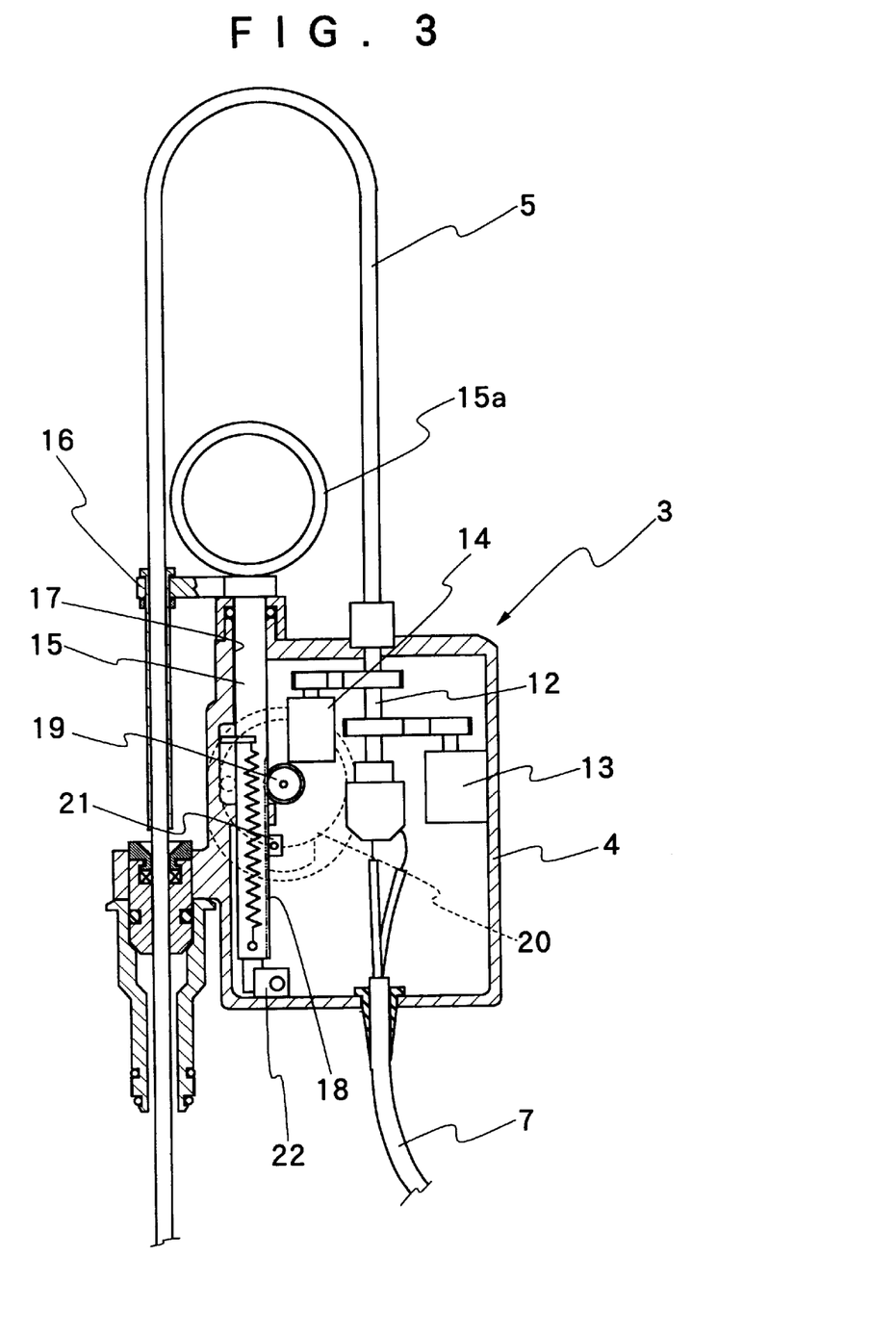
FIG. 3 is a schematic sectional view of a manipulating control head of the ultrasound probe.

Hereafter, the invention is described more particularly by way of its preferred embodiment with reference to the accompanying drawings. FIGS. 1 to 3 shows, as one example of 2D ultrasound image capture means, an ultrasound examination system employing an endoscopically inserting ultrasound probe.

In FIG. 1, indicated at 1 is an endoscope which is largely constituted by a manipulating or gripping head 1a and an elongated insertion rod 1b extended out on the front side of the gripping head 1a for insertion into patient body. Extended through the endoscope 1, from a fore end portion of the gripping head 1a to the distal end of the insertion rod 1b, is a biopsy channel 2 for insertion of forceps or other bioptic instruments. For this purpose, the biopsy channel 2 is opened to the outside at the distal end of the insertion rod 1b. Indicated at 3 is an ultrasound probe which is mounted on the gripping head 1a of the endoscope 1, the ultrasound probe 3 having a manipulating head assembly 4 and an elongated catheter member 5 to be introduced into a body cavity portion through the biopsy channel 2 of the endoscope 1. Led out on the rear side of the manipulating head assembly 4 is a connector cable 7 to be disconnectibly connected to an ultrasound image observation terminal 6 with a monitor screen 6b.

As shown in FIG. 2, the catheter member 5 has its component parts encased in a flexible tube 8 which is closed at its fore distal end. Namely, fitted in the flexible tube 8 is a flexible shaft 9 which consists of tightly wound coils and connected at its fore end to a support base 11 for a single-element ultrasound transducer 10 to transmit rotation thereto. In order to capture 2D ultrasound images sequentially, while pushing back and forth the catheter member 5 as a whole along a subject under observation, the flexible shaft 9 is turned about its axis within the flexible tube 8 to rotate the ultrasound transducer 10 together with the support base 11.

Further, as shown in FIG. 3, the rear or proximal end of the flexible shaft 9 is coupled with a rotational shaft 12 which is mounted within a manipulating head casing and coupled with a motor 13 and encoder 14 by way of pulleys and transmission belts or other coupling means. Accordingly, upon actuating the motor 13, its rotation is transmitted to the flexible shaft 9 through the rotational shaft 12. The rotational angle of the shaft 12 is detected by the encoder 14.

Further, provided on the manipulating head 4 is an operating rod 15 which is connected to a clamp member 16 to grip a proximal end portion of the catheter member 5, which is looped between an entrance opening at the proximal end of the biopsy channel 2 and the manipulating head assembly 4. The operating rod 15 is axially movable into and out of the casing of the manipulating head assembly 4 along a guide 17 to move the catheter member 5 in the linear or axial direction. Normally, the operating rod 15 is retained in an outer position projected outward of the manipulating head 4.

A rack 18 is provided on the operating rod 15 in meshed engagement with a pinion 19 which is connected to an encoder 20 for detection of linear or axial position of the ultrasound transducer 10 at the distal end of the catheter member 5. The operating rod 15 is provided with a finger holder ring 15a in which the operator can put his or her finger at the time of pushing or pulling the operating rod 15 into and out of the manipulating head assembly 4 for axial displacements of the catheter member 5. In FIG. 3, indicated at 21 and 22 are sensors which are provided within the manipulating control head 4 to detect inner and outer stroke ends of the operating rod 15.

Figure 4:
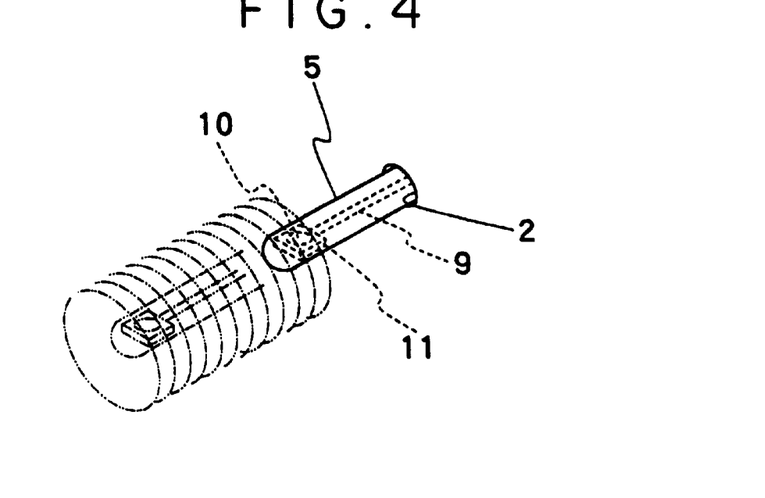
FIG. 4 is a schematic illustration explanatory of an ultrasound image capturing operation using the ultrasound probe.

With the ultrasound probe 3 arranged as described above, the ultrasound transducer 10 is put in rotation to make radial scans, driven from the motor 13. Signals of a 2D radial ultrasound image are obtained by a radial scan of the ultrasound transducer 10. If the axial position of the ultrasound transducer 10 at the distal end of the catheter member 5 is shifted little by little in an axial direction while making radial scans, by pulling the operating rod 15 in an inward or outward direction, a series of a large number (N-number) of 2D radial ultrasound images can be sequentially captured in a predetermined pitch in the axial direction as shown diagrammatically in FIG. 4.

Figure 5:
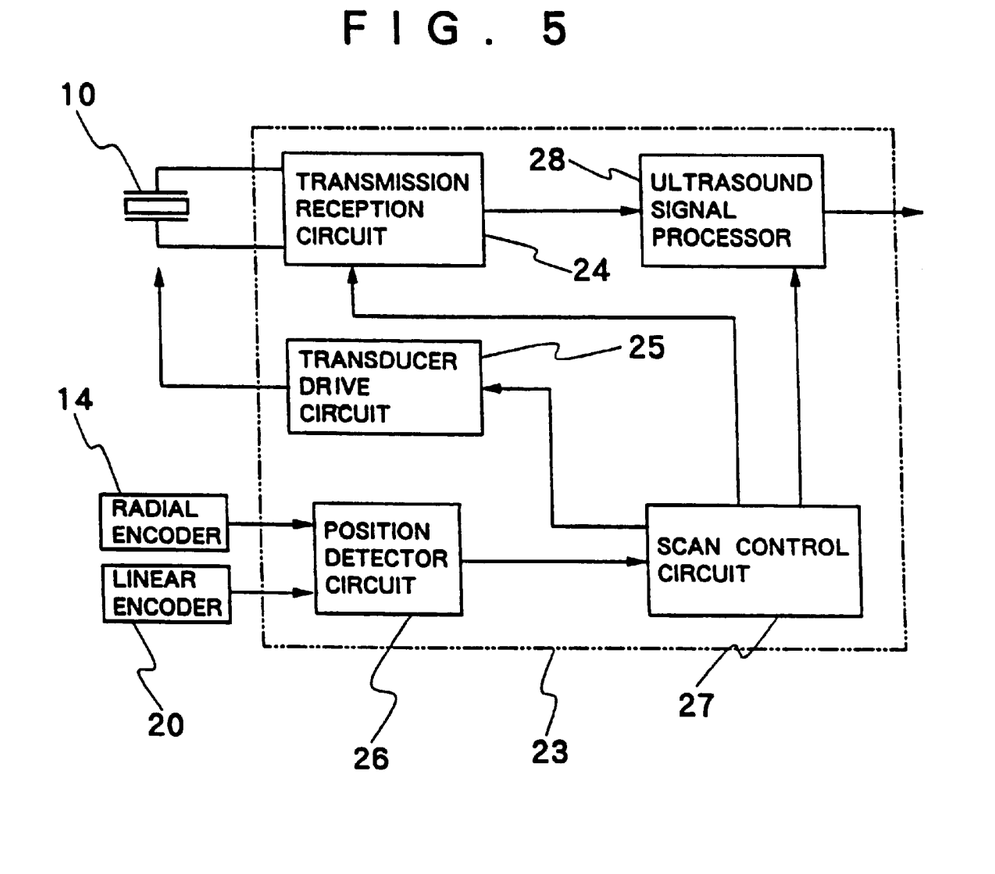
FIG. 5 is a block diagram of an ultrasound signal processor provided on the part of the ultrasound image capture device.

FIG. 5 shows the circuit arrangements of the ultrasound signal processor 6a on the ultrasound image observation terminal 6 which is connected to the ultrasound probe 3 as described above. The signal processor 6a includes a 2D ultrasound signal processing section 23 which is largely constituted by an ultrasound signal transmission/reception circuit 24, a transducer drive circuit 25, a position detecting circuit 26, an ultrasound scan control circuit 27 and an ultrasound signal processing circuit 28.

The ultrasound signal transmission/reception control circuit 24, which controls ultrasound signal transmission and reception by the transducer 10, is alternately switched between signal transmission and reception phases. In a signal transmission phase, according to trigger signals which are applied to the ultrasound transducer 10, ultrasound pulse signals are transmitted from the transducer 10 into an intracorporeal region of interest. After signal transmission for a predetermined time duration, the transmission/reception circuit 24 is switched into a signal reception phase to receive return echoes of the transmitted ultrasound pulse signals from various internal tissues of different acoustic impedances existing at different depths of a scanned sectional plane. Return echo signals received by the transducer 10 are converted into electric signals and transferred to the signal transmission/reception circuit 24.

The transducer drive circuit 25 controls the operation of the motor 13 which drives the ultrasound transducer 10, including on-off control on the motor 13 and control of its rotational speed to a predetermined constant level. The position detection circuit 26 detects the transducer position in the rotational direction, that is to say, the angular position of the ultrasound transducer 10 as well as its position in the axial direction. Therefore, the position detection circuit 26 determines the position of the ultrasound transducer 10 on the basis of position signals which are received from rotational angle detection encoder 14 and linear position detection encoder 20 and sensor 21.

The ultrasound scan control circuit 27 controls the ultrasound signal transmission/reception circuit 24 to generate trigger signals in each signal transmission phase, on the basis of angular position signals from the position detection circuit 26. Further, while transferring received ultrasound echo signals successively from the signal transmission/reception circuit 24 to the ultrasound signal processor circuit 28 to capture a series of a large number of 2D radial ultrasound images at linearly shifted positions, the axial position and the angular position in the rotational direction of the ultrasound transducer 10 need to be detected in relation with each acoustic line of the received echo signals. For this purpose, the linear and angular transducer position signals, detected by the position detection circuit 26 by way of the linear and angular position encoders 20 and 14, are also fed to the ultrasound signal processing section 28 as linear and axial position data along with the ultrasound echo signals from the signal transmission/reception circuit 24.

In each radial ultrasound scan, it is necessary to detect either an absolute position of the ultrasound transducer 10 or an initial position of a radial scan. In this regard, in view of simplicity in construction, the rotational angle detection encoder 14 is preferred to be an incremental encoder rather than an absolute encoder. This is because, even in the case of an incremental encoder, it is possible to provide an initial scan position indicator and to produce an initial scan position signal in addition to angular position signals of the ultrasound transducer 10. Accordingly, the position detection circuit 26 deals with angular position signal from the encoder 14, capture stroke start and end position signals from the sensors 21 and 22, and linear position signal from the encoder 20, for supply to the ultrasound signal processing section 28.

At the ultrasound signal processing circuit 28, 2D ultrasound images are successively generated on the basis of ultrasound echo signals from the signal transmission/reception circuit 24 and signals of radial scan reference position, angular position and linear position of the transducer received from the position detection circuit 26. In an image capturing, operation in a forward direction is started with a start position signal from the sensor 21 while operation in a reverse direction is started with an end position signal from the sensor 22. As a result, field image data of a large number of 2D ultrasound images are obtained in the forward capturing operation between the capture start position and the capture end position as well as in the reverse capturing operation between the capture end position and the capture start position. The field image data obtained in this manner by image capturing in the forward and reverse directions can be processed to generate a 3D ultrasound image although they are inverse to each other in direction order. In this instance, the ultrasound signal processing circuit 28 basically includes A/D converter and digital scan converter with a framing memory or the like to produce frames of video signals of 2D radial ultrasound picture images one after another.

Figure 6:
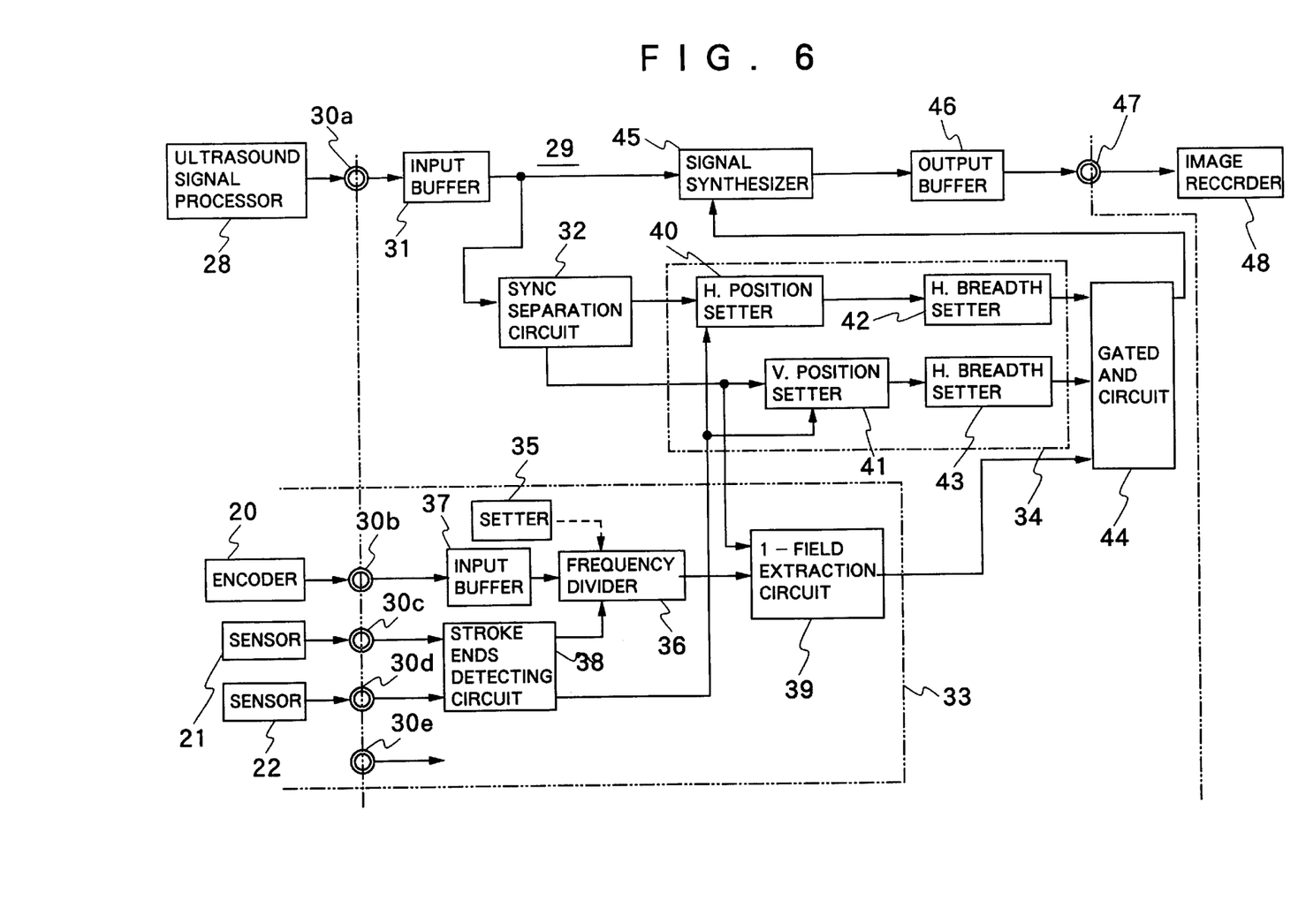
FIG. 6 is a block diagram of a marker section of an ultrasound image processing system according to the invention.

Connected to the ultrasound signal processing circuit 28 is a marker device 29 with circuit arrangements as shown in FIG. 6. The marker device 29 is provided with a plural number of terminals 30a to 30e, of which the terminal 30a is connected to the ultrasound signal processing circuit 28. The terminal 30b is connected to the encoder 20 which detects the linear position of the ultrasound transducer 10, while the terminals 30c and 30d are connected to the scan start position sensor 21 and the scan end position sensor 22, respectively. Further, the terminal 30e is a power supply terminal which is connected to a power source though not shown in the drawing. The output picture signals of 2D ultrasound images from the ultrasound signal processing circuit 28 are received at the terminal 30a and sequentially fed to a sync separation circuit 32 through an input buffer circuit 31 to pick up horizontal sync pulses (HD) and vertical sync pulses (VD).

Indicated at 33 is an image extracting section which selectively extracts 2D ultrasound images to be stamped with a marker signal, and at 34 is a marker signal generating section which generates marker signals to be stamped on selected 2D ultrasound images.

The image extracting section 33 includes a setter 35 for setting the rate of image extraction, for picking up and inserting a marker signal selectively at a desired rate on part of the field image data of the 2D ultrasound images which are sequentially fed to the marker inserting device 29. The setter 35 is connected to a frequency divider 36 so that the dividing frequency of the divider 36 can be set or altered by externally manipulating the setter 35. The frequency divider 36 is supplied with signals of linear position of the ultrasound transducer 10 from the encoder 20 through the input buffer circuit 37. By dividing the linear position signals from the encoder 20, the frequency divider 36 produces an extraction signals to insert a marker signal in field images of the sequentially received ultrasound images at a preset rate per unit distance of movement of the ultrasound transducer 10.

In an image capturing operation, the ultrasound transducer 10 is reciprocated in the linear direction between predetermined start and end positions, which also need to be detected. Besides, for 3D image processing, it is necessary to detect whether the ultrasound transducer 10 is in movement in the forward direction or in the reverse direction (whether the operating rod 15 is on an inward or outward stroke) because the order of the field images is reversed depending upon the capturing direction. The photoelectric sensors 21 and 22 are provided for detection of the start and end positions of the operating rod 15, and connected to the terminals 30c and 30d, respectively. Signals from these sensors 21 and 22 are fed to a capturing end detecting circuit 38 through the terminals 30c and 30d.

The sensors 21 and 22 detect the start and end positions of image capturing by the radial scan ultrasound transducer 10, which is reciprocated in the linear direction by the operating rod 15. Passage of the start position by the ultrasound transducer 10 is detected as the operating rod 15 is pushed in to block light to the sensor 21, while arrival of the ultrasound transducer 10 at the end position is detected as soon as the operating rod 15 comes to block the other sensor 22. When both of the sensors 21 and 22 are changed from an unblocked state to a blocked state, it means that the operating rod 15 is in movement in the forward direction. On the contrary, when both of the sensors 21 and 22 are changed from a blocked state to an unblocked state, it means that the operating rod 15 is in movement in the reverse direction. Therefore, in 3D image processing, the capturing end detecting circuit 38 serves to determine the length of a 3D ultrasound image to be generated, in addition to the detection of the above-mentioned direction of movement of the ultrasound transducer 10 in image capturing.

On the basis of the start and end position signals from the capturing end detecting circuit 38, the frequency divider 36 produces marker insertion command signals at preset intervals during the forward image capturing from the start to end position and also in the reverse image capturing from the end to start position.

In processing linear position signals, the image extracting section 36 does not necessarily operates in synchronism with the field image signals of captured 2D ultrasound images. For establishing synchronization with the latter, the image extracting section 36 is provided with a one-field extraction circuit 39 which is connected with the sync separation circuit 32 to receive vertical sync signals therefrom. A marking execution signal is produced by the one-field extraction circuit 39 when a vertical sync signal is received from the sync separation circuit 32 immediately after receipt of a marking command signal from the frequency divider 32.

The marker signal generating section 34, which serves to generate marker signals to be inserted into selected 2D ultrasound images, includes a horizontal position pointer 40 which designates horizontal marker positions on the basis of horizontal sync signals from the sync separation circuit 32, a vertical position pointer 41 which designates vertical marker positions on the basis of vertical sync signals from the sync separation circuit 32, a horizontal marker breadth setter 42, and a vertical marker breadth setter 43. Thus, according to the horizontal sync signal from the sync separation circuit 32, the position and breadth of a marker in the horizontal direction are determined by the horizontal position pointer 40 and horizontal breadth setter 42, and, according to the vertical sync signal, the position and breadth of the marker in the vertical direction are determined by the vertical position pointer 41 and vertical breadth setter 43. As a result, the range of marker area in both horizontal and vertical directions is determined at the marker generating section 34.

In inserting marker signals into 2D ultrasound images, it is preferable to change the marker position depending upon the direction of image capturing to distinguish 2D ultrasound images captured in the reverse direction from 2D ultrasound images captured in the forward direction. For this purpose, the signals indicative of the moving direction of the ultrasound transducer 10, which are produced by the capture end position detecting circuit 38 on the basis of the above-described start and end position signals, are fed to the horizontal and vertical position pointers 40 and 41 to change the horizontal and vertical positions of markers accordingly. In so doing, however, it is not necessary to change both of the horizontal and vertical positions. Namely, it suffices to change either the horizontal or vertical positions of the markers. Alternatively, the shape of the markers may be changed instead of the marker position.

The horizontal marker breadth setters 42 and 43 and the one-field extraction circuit 39 are connected to a gated AND circuit 44. Upon production of a marking execution signal by the one-field extraction circuit 39, the gate of AND circuit 44 is opened for a time duration corresponding to a time length of one field of picture signals, letting output signals of the horizontal and vertical marker breadth setters 42 and 43 pass through AND circuit 44 for synthesis of a marker signal. More specifically, the marker signals are fed to a marker synthesizer 45 thereby to synthesize a marker into a 2D ultrasound image.

Connected to an output terminal 47 is an image recording device 48 such as videotape recorder or the like. Thus, while capturing and processing 2D ultrasound images real-time by the ultrasound transducer 10 and the 2D ultrasound signal processor 28, field image data of captured 2D ultrasound images are sequentially recorded on the image recording device 48, with markers inserted at predetermined intervals or only in a selected number of field images per unit distance of image capturing movement to exclude other unmarked field images from three-dimensional image processing in a subsequent stage.

Picture data of a large number of 2D ultrasound images are saved in the image recording device 48 as a result of the above-described 2D ultrasound image capturing. On reading out these picture data for 3D image processing, only the field images which contain a marker signal are selectively extracted and fed to the 3D image processor to produce 3D voxel data or to produce a cut-out 3D ultrasound image with a cut-out section as will be described hereinbefore.

In ultrasound examinations, the catheter 5 of the ultrasound probe 3 is introduced into a body cavity through a biopsy or instrument channel 2 of an endoscope 3. To start ultrasound radial scans, the rotational shaft 12 is driven by the motor 13 to rotate the flexible shaft 9 about its longitudinal axis, whereupon the ultrasound transducer 10 which is connected to the distal end of the flexible shaft 9 is put in rotation while transmitting ultrasound pulses. Echo signals received by the ultrasound transducer 10 are transferred to the 2D ultrasound signal processor 23 on the ultrasound image observation terminal 6 to undergo predetermined signal processing operations which are known in the art.

As the operating rod 15 is pushed in, the ultrasound transducer 10 is moved in the linear direction while capturing radial ultrasound images. This movement of the ultrasound transducer 10 is detected by the encoder 20 to make radial ultrasound scans in a predetermined pitch or at predetermined intervals in the linear direction. Captured 2D ultrasound images are sequentially transferred from the signal processing circuit 28 of the 2D ultrasound signal processor 23 to the marker device 29. Concurrently, position signals from the encoder 20 and sensors 21 and 22 are also fed to the marker device 29. As shown particularly in FIG. 7(a), horizontal sync signals (HD) and vertical sync signals (VD) are separated from the 2D radial ultrasound image signals by the sync separation circuit 32.

Figure 7:
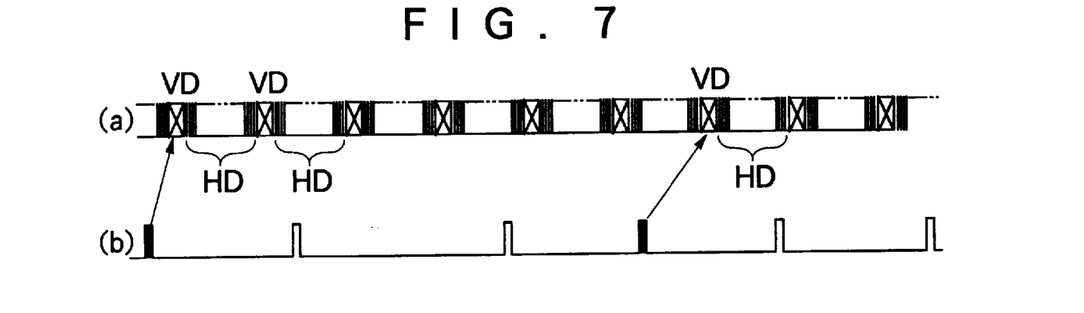
FIG. 7 is a diagrammatic illustration of marker positions in a series of sequentially captured 2D ultrasound images.

On the other hand, as shown in FIG. 7(b), while the probe operating rod 15 is being moved, the encoder 20 produces a pulse signal on every probe movement over a predetermined distance to detect the position of the ultrasound transducer 10 in the linear direction.

Further, during image capturing operations, the start and end positions of the forward and reverse strokes of the operating rod 15 are detected by the sensors 21 and 22 which are located at the outer and inner stroke ends of the operating rod 15, respectively. On the basis of these signals, a forward start pulse signal is produced by the capture end position detecting circuit 38 when the operating rod 15 is operated to move the ultrasound transducer 10 in a forward direction, turning the sensor 21 from unblocked state to blocked state. A pulse signal indicative of the end of the forward stroke is produced as soon as the ultrasound transducer 10 reaches the end position to change both of sensors 21 and 22 into blocked state. Further, a pulse signal indicative of the start of a reverse movement of the ultrasound transducer 10 is produced when both of the sensors 21 and 22 are turned into unblocked state from blocked state, and a pulse signal indicative of the end of a reverse movement is produced when both sensors 21 and 22 remain in unblocked state.

The start signals of image capturing in the forward and reverse directions are fed to the frequency divider 36 along with signals of linear position of the ultrasound transducer 10 from the encoder 20 to produce a marking command signal D which divides the linear position signals at a preset rate, for example, at a rate of ⅓ and outputs a marking command signal to the one-field extraction circuit 39 on every three pulses as shown in FIG. 7(b). The one-field extraction circuit which is supplied with vertical sync signals from the sync separation circuit 32 produces a marker insertion signal in response to a first vertical sync signal (VD) after reception of the marking command signal from the divider 36.

On the other hand, the horizontal and vertical position pointers 40 and 41 are supplied with the horizontal and vertical sync signals from the sync separation circuit 32, respectively, in addition to signals from the capturing end detecting circuit 38, to determine marker position and area within each extracted field of image.

Figure 8:
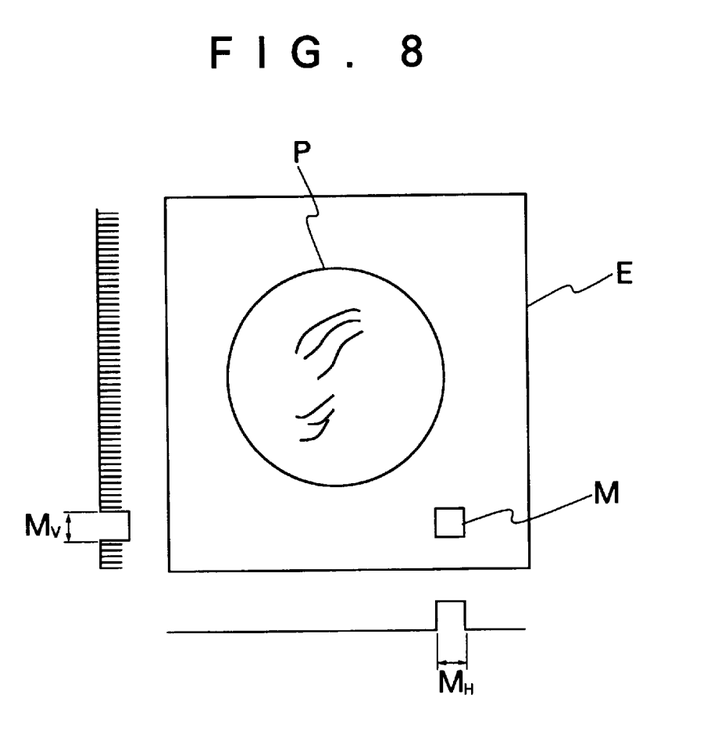
FIG. 8 is a timing chart of output signals from a marker signal generator.

More specifically, within a field of image having an area E as shown in FIG. 8, a marker M is inserted in a blank area outside a center region P which is occupied by a 2D ultrasound image. In order to insert the marker M in that position, it is necessary to specify its ranges in horizontal and vertical directions within the entire image area E. For this purpose, an initial marker write-in position in horizontal return time is determined by the horizontal position pointer 40, and its horizontal breadth is determined by the horizontal breadth setter 42. As a result, the horizontal position and breadth of the marker M are determined as indicated at $M_H$ in FIG. 8. On the other hand, an initial marker write-in position in a vertical return time is determined by the vertical marker position pointer 41, and vertical breadth of the marker is set by the vertical breadth setter 43. As a result, the vertical position and breadth of the marker are determined as indicated at $M_V$ of FIG. 8. In this instance, the marker position on 2D ultrasound images is changed depending upon the direction of movement of the ultrasound transducer 10, that is to say, depending upon the image capturing direction. Therefore, the horizontal and vertical marker position pointers 40 and 41 are arranged to change the initial marker write-in position on the basis of start and end position signals from the capture end detecting circuit 38, and the horizontal and vertical breadth setters 42 and 43 are arranged to produce signals of a fixed breadth irrespective of the direction of movement of the ultrasound transducer 10.

The above-described signals of initial marker write-in positions as well as the signals of marker breadth are generated on transfer of each 2D ultrasound image and sent to AND circuit 46. However, the gate of AND circuit 46 is opened to pass these signals to the signal synthesizer 45 only when a marker insertion signal is outputted from the one-field extraction circuit 39. Consequently, a marker is inserted into extracted 2D ultrasound images. Through output buffer circuit 46, the marked 2D ultrasound image is recorded in the image recording device 48 which is connected to output terminal 47, along with other unmarked 2D ultrasound images.

A large number of 2D ultrasound images which have been obtained by the real-time capturing can be processed into a 3D ultrasound image for display on a monitor screen. For 3D image processing, there have been developed and known in the art a number of methods, for example, a method of generating a 3D ultrasound image with a cut-out section by a 3D image processor as shown in FIG. 9.

Figure 9:
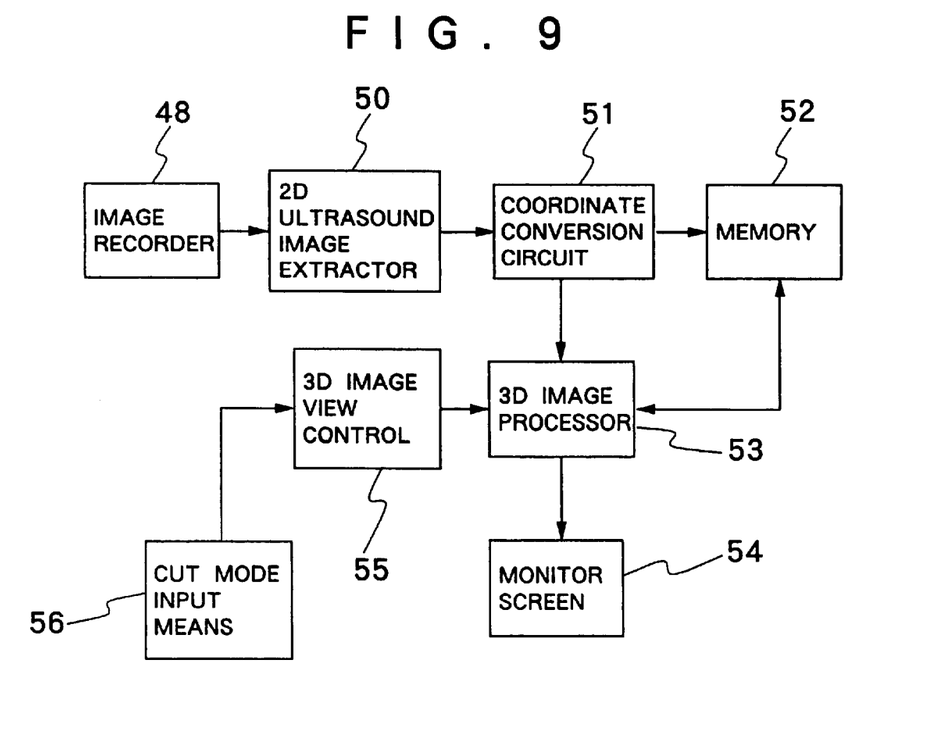
FIG. 9 is a circuit diagram of an exemplary 3D ultrasound image processor.

In FIG. 9, indicated at 50 is an image extractor for selectively extracting marked 2D ultrasound images alone, out of a large number of ultrasound images captured and saved in the recording device 48. N-number of extracted 2D ultrasound images are fed to a coordinate conversion circuit 51 and thereby converted into unit images as picture data for a 3D ultrasound image to be built up. Namely, at the coordinate conversion circuit 51, picture data of each 2D ultrasound image are put on a 3D coordinate system having X-, Y- and Z-axes which are disposed at 120 degrees with each other. The coordinate-converted picture data of the unit images are stored in a memory 52 and processed by a 3D image processor 53 to display a 3D ultrasound image on a viewing screen 54. In this instance, firstly a cylindrical 3D ultrasound image is generated by the 3D image processor 53 and displayed on the viewing screen 54. This 3D image is a surface image showing boundary surfaces of a scanned range, and also stored in the memory 52.

Connected to the 3D image processor 53 is a 3D image view control circuit 55 which is in turn connected to a cut surface input means 56, for example, in the form of a mouse or the like. As soon as cut mode and position are selected by way of the cut surface input means 56, necessary settings are made by the 3D image view control circuit 55 for picture data of a cut surface or surfaces to be shown in the selected mode and position on the 3D ultrasound image on display on a viewing screen. According to resulting picture data settings for cut surfaces, necessary picture data are read into the 3D image processor 53 from the memory 52 and pasted on the original 3D ultrasound image concurrently with data processing for surfaces to be concealed behind the pasted cut surfaces, displaying on a monitor screen 54, for example, a cut-out 3D ultrasound image I having cut surfaces $C_1$, $C_2$ and $C_3$.

Figure 10:
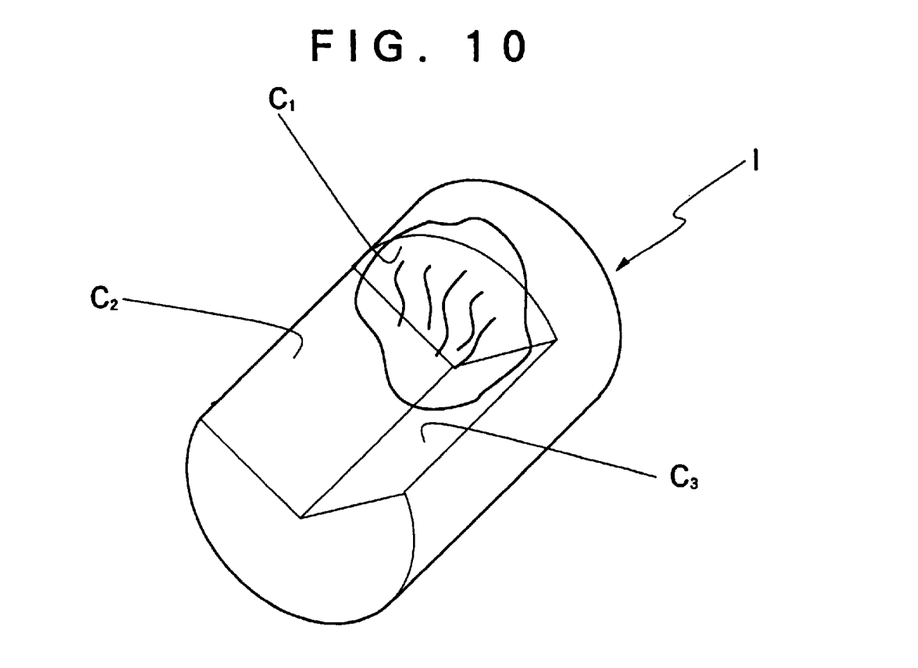
FIG. 10 diagrammatically shows a cut-out 3D ultrasound image as an example of 3D ultrasound image displayed on a monitor screen for examination of internal structures.

For generating a cut-out 3D ultrasound image of this sort, a marker is inserted into two-dimensional ultrasound images during the above-described real-time image capturing operation at a suitable dividing rate depending upon the resolution required for the 3D image. Namely, the resolution of ultimate 3D images can be easily changed by altering the setting of the frequency divider 35. It follows that the number of unit images for a cut-out 3D ultrasound image like the one as shown in FIG. 10 can be set arbitrarily, reducing the number of marked unit images to speed up the image processing when close examination is not necessary and increasing the number of marked unit images when a high resolution image is required for close examination.

What is claimed is:

1. An ultrasound image processing system, comprising:

an ultrasound probe including an ultrasound transducer configured to provide 2D scans over a predetermined range, and a drive means for moving said ultrasound transducer in a direction different from a direction of the 2D scans by said transducer;

a 2D ultrasound image capture means arranged to generate 2D ultrasound images by processing return echo signals received by said ultrasound transducer in a predetermined pitch in a direction of movement of said ultrasound transducer;

an image selector means arranged to select and extract unit 2D ultrasound images for 3D image processing from 2D ultrasound images sequentially generated by said 2D image capture means at a predetermined extraction rate in relation with movement of said ultrasound transducer;

a marker means for inserting a marker sign on frames of selected unit 2D ultrasound images outside an image area within a field of a selected 2D ultrasound image in relation with a picture signal processing operation by said 2D ultrasound image capture means; and an image recording means for storing 2D ultrasound images with a marker sign along with other non-selected 2D ultrasound images without a marker sign.

2. An ultrasound image processing system as defined in claim 1, wherein said ultrasound image capture means includes a radial scan type ultrasound transducer configured to scan radially and a linear drive means for moving said ultrasound transducer linearly back and forth in a direction perpendicular to radial planes of the radial scans.

3. An ultrasound image processing system as defined in claim 2, wherein said linear drive means includes means for detecting a position of said ultrasound transducer in said linear direction, and means for detecting start and end positions in said linear direction in order to detect the direction of movement of said ultrasound transducer while in an image capturing operation back and forth in said linear direction.

4. An ultrasound image processing system as defined in claim 3, wherein said marker means is configured to insert a marker of a different nature in ultrasound images captured and selected while said ultrasound transducer is in a forward movement in said linear direction than a marker sign to be inserted in ultrasound images captured and selected while in a reverse movement.

5. An ultrasound image processing system as defined in claim 1, wherein said marker means includes an image extraction circuitry for extracting 2D ultrasound images selectively at a preset rate, a marker signal generator for generating marker signals to be inserted into specified positions of extracted 2D ultrasound images, and a signal synthesizer for synthesizing marker signals with picture signals of said extracted ultrasound images.

6. An ultrasound image processing system as defined in claim 5, wherein said marker means includes a setting means for varying a rate of image extraction per unit distance of movement of said ultrasound transducer.

7. An ultrasound image processing system as defined in claim 1, wherein said marker means is provided with a one-field extraction circuit and a divider, and arranged to execute marking when a vertical sync signal is outputted from said one-field extraction circuit.

8. An ultrasound image processing system as defined in claim 1, wherein said image recording means is selected from a group consisting of a video memory, a videotape recorder, a magnetic disc, a photomagnetic disc and an optical disc.

9. An ultrasound image processing system as defined in claim 1, further comprising a 3D image processor for generating a 3D ultrasound image on the basis of picture data of marked 2D ultrasound images selectively picked from a number of 2D ultrasound images stored in said image recording means.

10. An ultrasound image processing system as defined in claim 9, wherein said 3D image processor includes a 3D signal processor and a view control to display on a monitor screen a cut-out 3D ultrasound image having a cut-out portion in a selected region to expose internal structures to view.

11. An ultrasound image processing system as defined in claim 1, wherein said ultrasound image capture means is an ultrasound probe to be introduced into a body cavity through an endoscopic instrument channel.

12. An ultrasound image processing system, comprising:
an ultrasound probe comprising,
an ultrasound transducer configured to provide 2D scans over a predetermined range, and
a motor configured to move said ultrasound transducer in a direction different from a direction of the 2D scans by said transducer;
a signal processing circuit configured to generate 2D ultrasound images by sequentially processing return echo signals received by said ultrasound transducer in a predetermined pitch in a direction of movement of said ultrasound transducer;
an image extracting section configured to select and extract unit 2D ultrasound images for 3D image processing from 2D ultrasound images sequentially generated by said signal processing circuit at a predetermined extraction rate in relation with movement of said ultrasound transducer;
a marker device configured to insert a marker sign on frames of selected unit 2D ultrasound images outside an image area within a field of a selected 2D ultrasound image in relation with a picture signal processing operation by said signal processing circuit; and
a memory device configured to store 2D ultrasound images with a marker sign along with other non-selected 2D ultrasound images without a marker sign.

* * * * *